(12) United States Patent
Ron et al.

(10) Patent No.: US 7,306,905 B2
(45) Date of Patent: Dec. 11, 2007

(54) METHOD OF IDENTIFYING SUBSTANCES USEFUL FOR PROMOTING RESISTANCE TO CELL STRESS

(75) Inventors: David Ron, New York, NY (US); Heather P. Harding, Brooklyn, NY (US)

(73) Assignee: New York University, New York, NY (US)

( * ) Notice: Subject to any disclaimer, the term of this patent is extended or adjusted under 35 U.S.C. 154(b) by 738 days.

(21) Appl. No.: 10/150,759

(22) Filed: May 17, 2002

(65) Prior Publication Data

US 2003/0008272 A1    Jan. 9, 2003

Related U.S. Application Data

(60) Provisional application No. 60/292,054, filed on May 18, 2001.

(51) Int. Cl.
*C12Q 1/68* (2006.01)
*C12Q 1/00* (2006.01)

(52) U.S. Cl. ................... 435/6; 435/4; 435/29
(58) Field of Classification Search ............ None
See application file for complete search history.

(56) References Cited

U.S. PATENT DOCUMENTS

| | | | | |
|---|---|---|---|---|
| 5,089,397 | A * | 2/1992 | Kushner et al. | 435/69.1 |
| 5,770,430 | A * | 6/1998 | Howell et al. | 435/325 |
| 6,013,623 | A | 1/2000 | Spector et al. | 514/6 |
| 6,048,709 | A | 4/2000 | Falb | 435/69.1 |
| 6,120,994 | A * | 9/2000 | Tam | 435/6 |
| 6,331,396 | B1 | 12/2001 | Silverman et al. | 435/6 |
| 6,344,324 | B2 | 2/2002 | Howell et al. | 435/6 |
| 2002/0039791 | A1 | 4/2002 | Austin et al. | 435/456 |

OTHER PUBLICATIONS

Wang et al. Identification of novel stress-induced genes downstream of chop. EMBO J. vol. 17, No. 13, pp. 3619-3630, Jul. 1998.*
Lin et al. Quantification of tumor cell injury in vitro and in vivo using expression of green fluorescent protein under the control of the GADD153 promoter. Int J Cancer. vol. 91, No. 4, pp. 555-562, Feb. 2001.*
Wang et al. Cloning of mammalian Ire1 reveals diversity in the ER stress responses. EMBO J. vol. 17, No. 19, pp. 5708-5717, Oct. 1998.*
Zhang et al. Cancer-preventive isothiocyanates: dichotomous modulators of oxidative stress. Free Radic Biol Med. vol. 38, No. 1, pp. 70-77, Jan. 2005.*
MeSH entry for "Prion Diseases", printed Feb. 15, 2006.*
Silva et al. CHOP/GADD153 is a mediator of apoptotic death in substantia nigra dopamine neurons in an in vivo neurotoxin model of parkinsonism. J Neurochem. vol. 95, No. 4, pp. 974-986, 2005.*
Moreau. Heme oxygenase: protective enzyme or portal hypertensive molecule? Journal of Hepatology. vol. 34, pp. 936-939, 2001.*
GenBank Accession No. AA049696, GI: 1529366, Sep. 9, 1996.*
Kanai et al. Expression cloning and characterization of a transporter for large neutral amnio acids activated by the heavy chain of 4F2 antigen (CD98). The Journal of Biological Chemistry, vol. 273, No. 37, pp. 23629-23632, 1998.*
Sullivan et al. Insulin induces dephosphorylation of eukaryotic initiation factor 2alpha and restores protein synthesis in vulnerable hippocampal neurons after transient brain ischemia. Journal of Cerebral Blood Flow and Metabolism, vol. 19, pp. 1010-1019, 1999.*
Guyton et al. Induction of the mammalian stress response gene GADD153 by oxidative stress: role of AP-1 element, Biochem J. vol. 314, pp. 541-554, 1996.*
Leuthy et al. Isolation and characterization of the hamster gadd153 gene. The Journal of Biological Chemistry. vol. 265, No. 27, pp. 16521-16526, 1990.*
GenBank Accession No. S40707, GI: 252003, May 8, 1993.*
Hoshida et al. Effects of preconditioning with ebselen on glutathione metabolism and stress protein expression. The Journal of Pharmacology and Experimental Therapeutics, vol. 281, No. 3, pp. 1471-1475, 1997.*
Kim et al. Significance analysis of lexical bias in microarray data. BMC Bioinformatics, vol. 4, p. 12, 2003.*
Bertolotti et al., "Dynamic Interaction of BiP and ER Stress Transduction in the Unfolded-Protein Response", *Nature Cell Biol.*, 2:326-332 (2000).
Dudek et al., "Essential Amino Acids Regulate Fatty Acid Synthase Expression through an Uncharged Transfer RNA-dependent Mechanism", *J. Of Biol. Chem.*, 270:29323-29329 (1995).
Harding et al., "Diabetes Mellitus and Exocrine Pancreatic Dysfunction in Perk-/-Mice Reveals A Role for Translational Control in Survival of Secretory Cells", *Mol Cell.*, 7:1153-63 (2001).
Harding et al., "Protein Translation and Folding are Coupled By an Endoplasmic-Reticulum-resident Kinase", *Nature*, 397:271-274 (1999).
Harding et al., "Regulated translation initiation controls stress-induced gene expression in mammalian Cells", *Mol, Cell*, 6:1099-1108 (2000).
Harding et al., "Perk is essential for translational regulation and cell survival during the unfolded protein response", *Mol, Cell*, 5:1-20 (2000).
Hettmann et al., "Microphthalmia due to p53-mediated apoptosis of anterior lens epithelail cells in mice lacking the CREB-2 transcription factor", *Dev. Biol.* 222:110-123 (2000).
Kaufman R., "Stress signaling from the lumen of the endoplasmic reticulum: coordination of gene transcriptional and translational controls", *Genes and Dev.*, 13:1211-1233 (1999).

(Continued)

Primary Examiner—Celine Qian
Assistant Examiner—Jennifer Dunston
(74) Attorney, Agent, or Firm—Darby & Darby P.C.

(57) ABSTRACT

The invention is directed to methods for identifying test substances useful for the prevention or treatment of diseases involving an oxidative stress. The methods involve screening assays, including high throughput screening techniques, in which the test substances are tested for their ability to promote resistance to oxidative stress by activating one or more points of the integrated stress response pathway, while not causing stress.

6 Claims, 2 Drawing Sheets

OTHER PUBLICATIONS

Figure 1:
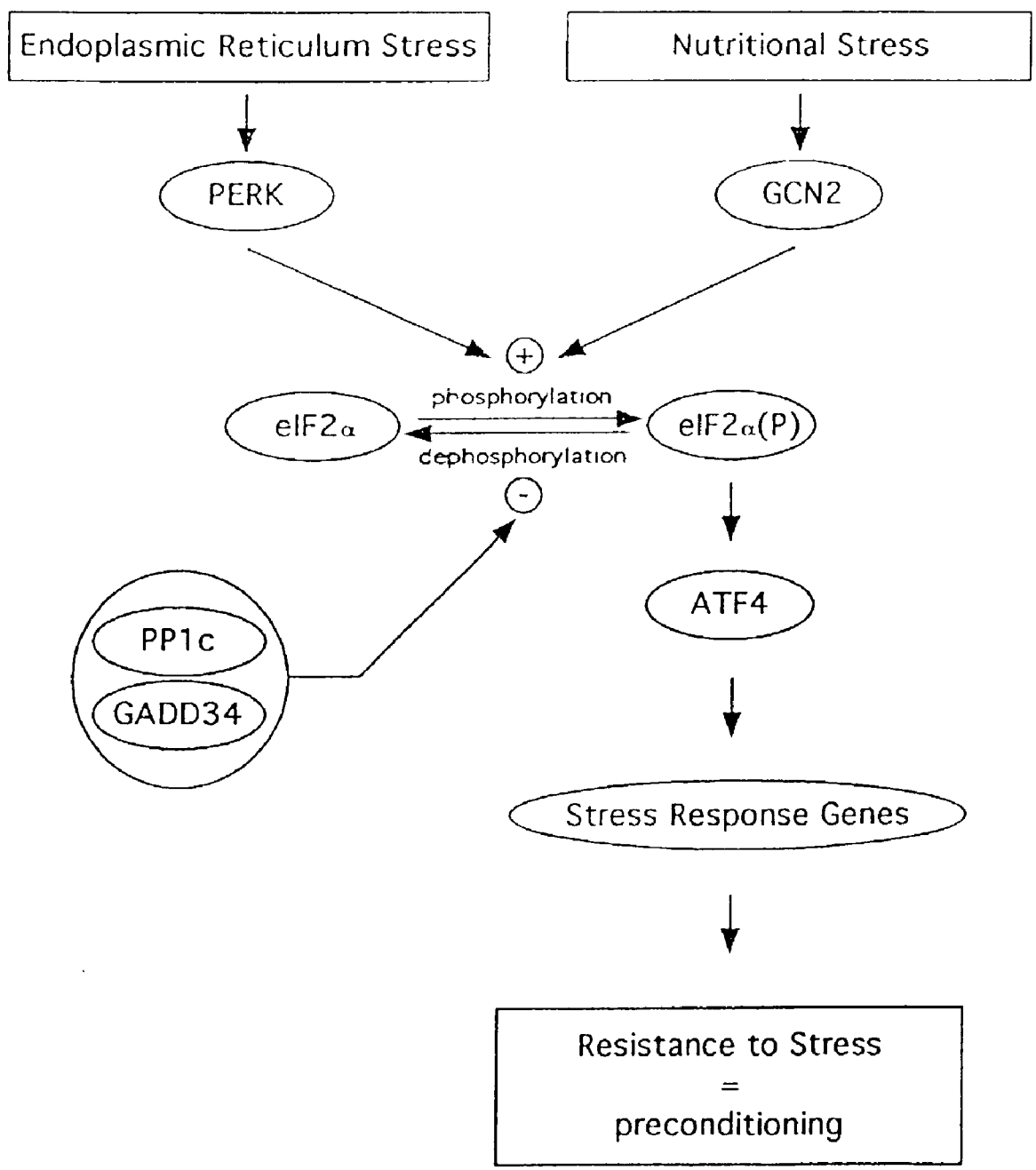

Kimball et al., "Implication of eIF2B Rather Than eIF4Ein the Regulation of Global Protein Synthesis by Amino Acids in L6 Myoblasts", *J. Of Biol. Chem*, 273:30945-30953 (1998).

Novoa et al., "Feedback inhibition of the unfolded protein response by GASS34-mediated dephosphorylation of eIR2α", *J. Cell. Biol.*, 153:1011-1022 (2001).

Wang et al., "Activation of ATF6 and an ATF6DNA Binding Site by the Endoplasmic Reticulum Stress Response", *J. Of Biol. Chem.*, 275:27013-27020 (2000).

Wang et al., "Cloning of mammalian Irel reveals diversity in the ER stress responses", *EMBO Journal*, 17:5708-5717 (1998).

Brown and Bickenell, "Hypoxia and oxidative stress in breast cancer. Oxidative stress: its effects on the growth, metastatic potential and response to therapy of breast cancer", Breast Cancer Res, 2001; 3, 323-327.

de las Alas, et al, "Increases in tumor GADDD153 mRNA level following correlates with response to paclitaxel", Cancer Chemother Pharmacol, 2000; 45:381-388.

Gerwitz, "A critical evaluation of the mechanisms of action proosed for the antitumor effects of the anthracycline antibiotics adriamyoin and daunorubicin", Biochem Pharmacol, 1999; 57:727-741.

Kang, "Oxidative stress, DNA damage, and breast cancer", 2002; 13:540-549.

Toyokuni, et al., "Persistent oxidative stress in cancer", FEBS Lett, 1995; 358:1-3.

\* cited by examiner

METHOD OF IDENTIFYING SUBSTANCES USEFUL FOR PROMOTING RESISTANCE TO CELL STRESS

This application claims the benefit of priority under 35 U.S.C. §119 based upon Ser. No. 60/292,054, filed May 18, 2001, the entire disclosure of which is incorporated herein by reference.

Numerous references, including patents, patent applications, and various publications are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

This invention was made with Government support under Grant No. ES08681 awarded by the NIEHS and Grant No. DK47119 awarded by NIDDK. The United States Government may have certain rights to this invention pursuant to these grants.

1. FIELD OF INVENTION

The invention is directed to methods for identifying test substances useful for the prevention or treatment of diseases involving an oxidative stress. The methods involve screening assays, including high throughput screening techniques, in which the test substances are tested for their ability to promote resistance to oxidative stress by activating one or more points of the integrated stress response pathway, while not causing stress.

2. BACKGROUND OF INVENTION

Primary reactive oxygen species (ROS) such as superoxide radical, hydrogen peroxide, hydroxyl radicals, and ortho-quinone derivatives of catecholamines exert their cellular effects by modifying DNA, lipids, and proteins to form secondary electrophiles. Examples of such latter secondary electrophiles include hydroxyalkenals, nucleotide propenals, and hydroxyperoxy fatty acyl chains. The secondary electrophiles are implicated in cellular dysfunction either because they are no longer able to participate in normal cellular activity or because they serve as electron acceptors in oxidative chain reactions that result in the modification of other essential cellular components. Damage caused by the primary and secondary ROS contributes to the pathogenesis of important human disease caused by neuronal ischemia during stroke, post-cardiopulmonary bypass syndrome, brain trauma, and status epilepticus. ROS likely participate in cardiac damage induced during ischemic heart disease, renal damage induced by ischemia and toxins as well as in more chronic diseases such as the destruction of the islets of Langerhans of the endocrine pancreas in Diabetes Mellitus, the destruction of neurons in Parkinson's disease, and other chronic neurodegenerative disorders.

One way that cells handle the deleterious effects of ROS is through a preconditioning response. The preconditioning response is an adaptation whereby cells are rendered resistant to injury by prior exposure to smaller doses of the same stress, which threatens to cause the injury in question. It is highly problematic to screen for potential therapeutics that cause the preconditioning response, since compounds that are identified as causing the preconditioning response generally also cause stress on the cell.

The accumulation of malfolded proteins in the endoplasmic reticulum leads to accumulation of reactive oxygen species. The protein kinase PERK has been shown to be activated by the stress of the accumulation of malfolded proteins in the endoplasmic reticulum (ER stress), and in turn phosphorylates the translation initiation factor eIF2α on its alpha subunit (Harding, H., Zhang, Y., and Ron, D. (1999). Translation and protein folding are coupled by an endoplasmic reticulum resident kinase. Nature 397, 271-274). A different eIF2α kinase, GCN2, has been also shown to phosphorylate eIF2α, however it acts in response to nutritional stress, not ER stress (Harding, H., Novoa, I., Zhang, Y., Zeng, H., Schapira, M., and Ron, D. (2000). Regulated translation initiation controls stress-induced gene expression in mammalian cells. Mol. Cell 6, 1099-1108). eIF2α phosphorylation leads to marked reduction in protein biosynthesis (Harding, H., Zhang, Y., Bertolotti, A., Zeng, H. and Ron, D. (2000). Perk is essential for translational regulation and cell survival during the unfolded protein response. Mol. Cell 5, 897-904) and to the expression of a transcription factor, ATF4, which then activates stress response genes in a signaling pathway termed the Integrated Stress Response (Harding, H., Novoa, I., Zhang, Y., Zeng, H., Schapira, M., and Ron, D. (2000). Regulated translation initiation controls stress-induced gene expression in mammalian cells. Mol. Cell 6, 1099-1108). This activation pathway is down-regulated by the activity of a phosphatase holoenzyme that dephosphorylates eIF2α on serine 51 (in yeast eIF2α, corresponding to residue 52 in rodents or humans). The phosphatase holoenzyme consists of the catalytic subunit of protein phosphatase 1 (PP1c) and GADD34, an eIF2α-specifc regulatory subunit of the phosphatase (Novoa, I.; Zeng, H., Harding, H., and Ron, D. (2001). Feedback inhibition of the unfolded protein response by GADD34-mediated dephosphorylation of eIR2α. J. Cell Biol., 153, 1011-1022).

This invention involves the discovery that the activation of stress response genes in the integrated stress response promotes resistance to both the stress of malfolded proteins in the endoplasmic reticulum and to the consequences of the accumulation of ROS. Therefore, the activation pathway of the integrated stress response pathway provides a desirable target for screening test substances capable of activating the pathway to promote preconditioning. Furthermore, screening test substances through the integrated stress response provides the advantage of identifying compounds, which activate the pathway, yet do not provide stress.

3. SUMMARY OF INVENTION

The invention is directed to a method for identifying a test substance useful for the prevention or treatment of a disease involving an oxidative stress, which comprises testing the substance for its ability to promote resistance to cell stress while not causing stress, so as to thereby determine whether said substance is effective as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of CHOP gene, and ii) identifying the test substance which activates the expression of CHOP, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of CHOP gene, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of GLYT1 gene, and ii) identifying the test substance which activates the expression of GLYT1, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of GLYT1 gene, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of cystathionine gamma-lyase, and ii) identifying the test substance which activates the expression of cystathionine gamma-lyase, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of cystathionine gamma-lyase, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of methylenetetrahydrofolate dehydrogenase, and ii) identifying the test substance which activates the expression of methylenetetrahydrofolate dehydrogenase, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of methylenetetrahydrofolate dehydrogenase, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of serine hydroxymethyltransferase, and ii) identifying the test substance which activates the expression of serine hydroxymethyltransferase, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of serine hydroxymethyltransferase, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of heme oxygenase-1, and ii) identifying the test substance which activates the expression of heme oxygenase-1, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of heme oxygenase-1, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of XCTc gene, and ii) identifying the test substance which activates the expression of XCTc gene, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of XCTc gene, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of coproporphyrinogen oxidase, and ii) identifying the test substance which activates the expression of coproporphyrinogen oxidase, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of coproporphyrinogen oxidase, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of a target gene, wherein the target gene is selected from the group consisting of Tj6 gene, Sec23b gene, Ugalt gene, 1500026A19Rik gene, Gpnat1 gene, Pig-a gene, Sel1h gene, Sel1l gene, WRN typeII gene, A170 gene, Prkri gene, Dnajc3 gene, Dnajb9 gene, mATF4 gene, LRG-21 gene, EST1 gene, Wars gene, 1110068E11Rik gene, Rnu22 RNA gene, GU2 gene, Snk gene, Fyn gene, 5730434I03RiK gene, Rnu22 RNA gene, GU2 gene, Snk gene, Fyn gene, 5730434I03Rik gene, Mpc2 gene, Ets-2 gene, c-myc gene, Arnt3 gene, E4BP4 gene, Etv6 gene, 2310004B05Rik gene, EST2 gene, Actb gene, Ghitm gene, EST3 gene, and Rnu1a-1 gene, and ii) identifying the test substance which activates the expression of the target gene, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of a target gene, wherein the target gene is selected from the group consisting of Tj6 gene, Sec23b gene, Ugalt gene, 1500026A19Rik gene, Gpnat1 gene, Pig-a gene, Sel1h gene, Sel11 gene, WRN typeII gene, A170 gene, Prkri gene, Dnajc3 gene, Dnajb9 gene, mATF4 gene, LRG-21 gene, EST1 gene, Wars gene, 1110068E11Rik gene, Rnu22 RNA gene, GU2 gene, Snk gene, Fyn gene, 5730434I03RiK gene, Rnu22 RNA gene, GU2 gene, Snk gene, Fyn gene, 5730434I03Rik gene, Mpc2 gene, Ets-2 gene, c-myc gene, Arnt3 gene, E4BP4 gene, Etv6 gene, 2310004B05Rik gene, EST2 gene, Actb gene, Ghitm gene, EST3 gene, and Rnu1a-1 gene, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of a target gene, wherein said target gene may be identified in a assay comprising submitting a cell to stressful conditions and determining the genes whose transcription is enhanced in the presence of an active PERK protein and not enhanced or inhibited in the absence of such active PERK protein, and ii) identifying the test substance which activates the expression of said target gene, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of a target gene, wherein said target gene may be identified in a assay comprising submitting a cell to stressful conditions and determining the genes whose transcription is enhanced in the presence of an active PERK protein and not enhanced or inhibited in the absence of such active PERK protein, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of a target gene, wherein said target gene may be identified in a assay comprising submitting a cell to stressful conditions and determining the genes whose transcription is enhanced in the presence of an active GCN2 protein and not enhanced or inhibited in the absence of such active GCN2 protein, and ii) identifying the test substance which activates the expression of said target gene, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of a target gene, wherein said target gene may be identified in a assay comprising submitting a cell to stressful conditions and determining the genes whose transcription is enhanced in the presence of an active GCN2 protein and not enhanced or inhibited in the absence of such active GCN2 protein, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of a target gene, wherein said target gene may be identified in a assay comprising submitting a cell to stressful conditions and determining the genes whose transcription is enhanced in the presence of an active ATF4 protein and not enhanced or inhibited in the absence of such active ATF4 protein, and ii) identifying the test substance which activates the expression of said target gene, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of a target gene, wherein said stress response gene may be identified in a assay comprising submitting a cell to stressful conditions and determining the genes whose transcription is enhanced in the presence of an active ATF4 protein and not enhanced or inhibited in the absence of such active ATF4 protein, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of ATF4 gene, and ii) identifying the test substance which activates the expression of ATF4, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate the expression of ATF4 gene, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to increase phosphorylation of eIF2α, and ii) identifying the test substance which increases phosphorylation of eIF2α, thereby to identify a test substance useful as a preventive or therapeutic agent for a disease involving an oxidative stress. The invention is further directed to a method for identifying a test substance useful for the prevention or treatment of a disease involving an oxidative stress, which comprises testing a test substance for its ability to increase phosphorylation of eIF2α, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to inhibit the dephosphorylation of eIF2α, and ii) identifying the test substance which inhibits the dephosphorylation of eIF2α, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to inhibit the dephosphorylation of eIF2α, thereby to determine whether the substance promotes resistance to cell stress, and to identify said substance as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate an eIF2α kinase and ii) identifying the test substance which activates an eIF2α kinase, thereby to identify a test substance useful as a preventive or therapeutic agent for a disease involving an oxidative stress. The invention is additionally directed to a method for identifying a test substance useful for the prevention or treatment of a disease involving an oxidative stress, which comprises testing a test substance for its ability to activate an eIF2α kinase, thereby to determine whether the substance promotes resistance to cell stress, and to identify said substance as a preventive or therapeutic agent for a disease involving an oxidative stress.

The invention is directed to a method for the prevention or treatment of a disease involving an oxidative stress in a patient in need of such treatment, which comprises administering to the patient an effective amount of a therapeutic agent identified for its ability to promote resistance to cell stress while not causing stress. The therapeutic agent enhances the activity of the Integrated Stress Response pathway.

4. BRIEF DESCRIPTION OF THE FIGURES

FIG. 1: Schematic description of a portion of the Integrated Stress Response.

Figure 2:
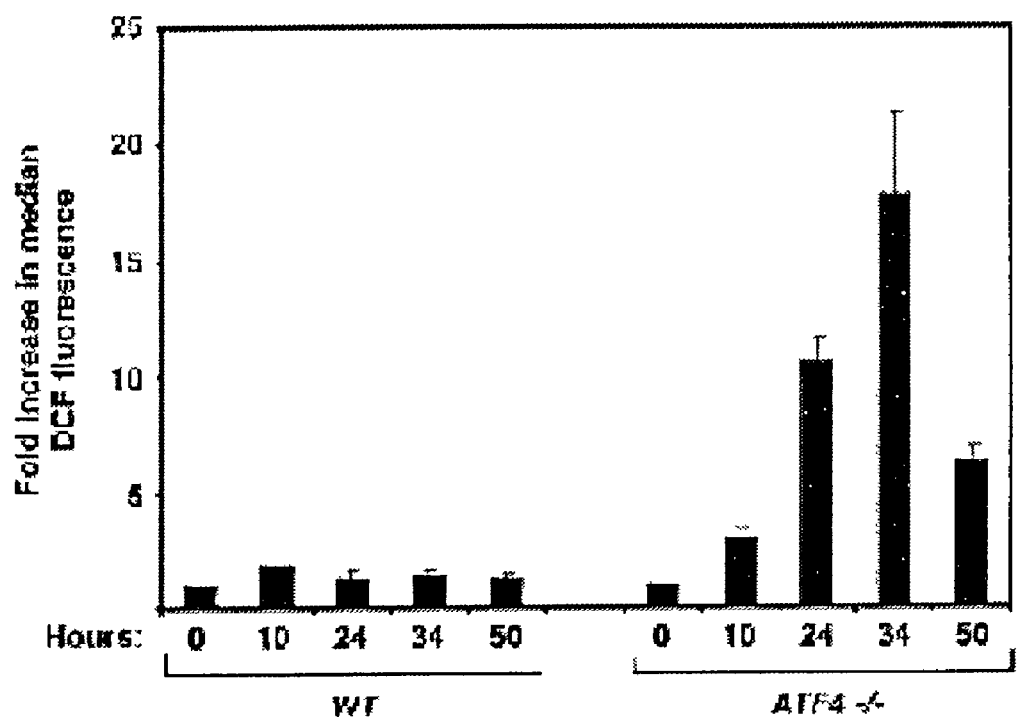
Figure 2:
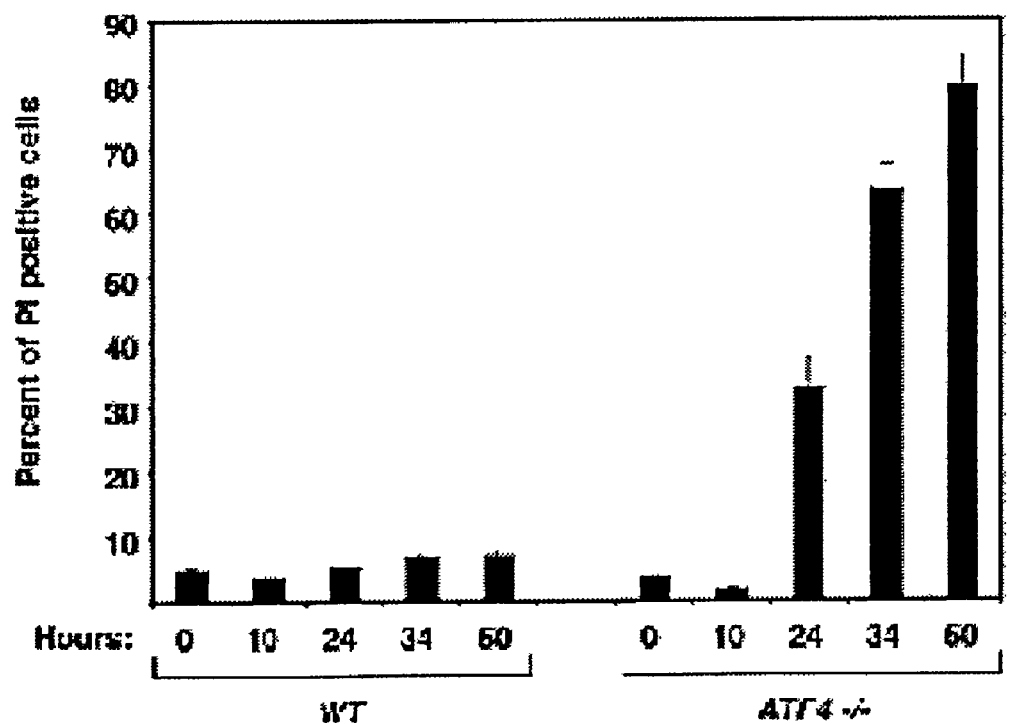

FIG. 2: ATF4−/− cells, that are defective in induction of the Integrated Stress Response, experience oxidative stress and cell death. (A) Fold-change in median DCF (dichlorofluorescein) fluorescence, detected by FACS analysis in live wildtype and ATF4−/− mouse fibroblasts after removal from protective, glutathione-containing media. DCF is a fluorescent probe that reports on the concentration of reactive oxygen species in the cell. The level of DCF fluorescence in cells growing in protective-glutathione-containing media is set at "1". (B) Percent of propidium iodide (PI) positive cells in the same samples shown in (A). PI uptake is a marker for loss of integrity of the cell membrane and cell death.

5. DETAILED DESCRIPTION OF THE INVENTION

Definitions

The terms used in this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Primary reactive oxygen species (ROS) include, but are not limited to, superoxide radical, hydrogen peroxide, hydroxyl radical, and ortho-quinone derivatives of catecholamines. Primary ROS exert their cellular effects by modifying DNA, lipids and proteins to form secondary electrophiles. The secondary electrophiles are also implicated in cellular dysfunction either because they are no longer able to participate in normal cellular activity or because they serve as electron acceptors in oxidative chain reactions that result in the modification of other essential cellular components. Examples of such latter secondary electrophiles or secondary reactive oxygen species include hydroxyalkenals, nucleotide propenals, and hydroxyperoxy fatty acyl chains.

Oxidative stress or stressful conditions involves any actions by primary or secondary reactive oxygen species on the body.

Cell stress includes oxidative stress, ER stress, and nutritional stress on the cell and any subsequent cell injury due to the initial oxidative stress, ER stress, and nutritional stress.

Diseases involving an oxidative stress have a pathogenesis related to the damage caused by the primary and secondary ROS. ROS contribute to the pathogenesis of important human diseases caused by neuronal ischemia during stroke, post-cardiopulmonary bypass syndrome, brain trauma, and status epilepticus. ROS likely participate in cardiac damage induced during ischemic heart disease, renal damage induced by ischemia and toxins as well as in more chronic diseases such as the destruction of neurons in Parkinson's disease, Amyloidoses, Prion disorders, Alzheimer's disease, and other chronic neurodegenerative disorders. Autoimmune diseases such as the destruction of the islets of Langerhans of the endocrine pancreas in Diabetes Mellitus are also encompassed.

Preconditioning is the effect in which a low dose of a stressful stimulus associated with oxidative stress promotes resistance to ROS. This effect is a natural cellular defense strategy to combat the effects of ROS.

Target gene and target protein are understood to refer to the gene or protein of the Integrated Stress Response pathway whose activation or inhibition is determined in the screening methods of the invention. The target genes or proteins are meant to refer to genes or proteins of any origin, regardless of the species. Substantially all the target genes or proteins used in the methods of the invention can be obtained from higher eukaryote organisms, such as mammalian or bird genes or proteins. They may more particularly be rodent or primate genes or proteins, preferably human. However certain of the genes or proteins used in the methods of the invention may alternatively be obtained from inferior organisms such as yeasts. They may have homologous wild-type sequences or be function-conservative variants. Function-conservative variants are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A function-conservative variant also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term homologous in all its grammatical forms and spelling variations refers to the relationship between proteins that possess a "common evolutionary origin," and homologous proteins from different species. Such proteins (and their encoding genes) have sequence homology, as reflected by their sequence similarity, whether in terms of percent similarity or the presence of specific residues or motifs at conserved positions. Accordingly, the term sequence similarity in all its grammatical forms refers to the degree of identity or correspondence between nucleic acid or amino acid sequences of proteins that may or may not share a common evolutionary origin. In a specific embodiment, two DNA sequences are substantially homologous or substantially similar when at least about 80%, and most preferably at least about 90 or 95%) of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system. Similarly, in a particular embodiment, two amino acid sequences are substantially homologous or substantially similar when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is hybridizable to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. In a specific embodiment, the term standard hybridization conditions refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions. Sequence-conservative variants are also encompassed. These are gene variants in which a change of one or more nucleotides in a given codon position results in no alteration in the amino acid encoded at that position.

Expression of a gene is understood to include both transcription and/or translation events.

Test substance is a chemically defined compound or mixture of compounds (as in the case of a natural extract or tissue culture supernatant) whose ability to promote resistance to cell stress, while not causing stress, is defined by the assays of the invention.

Methods

The screening methods of the invention are directed to different activation sites of the Integrated Stress Response, which includes, but is not limited to, the components illustrated in FIG. 1. The methods include:

1) Activated expression of target genes included in Tables 1 and 2, ATF4, also known as CREB2, TAXREB67, and C/ATF4 (Harding, H., Novoa, I., Zhang, Y., Zeng, H., Shapira, M., and Ron, D. (2000). Regulated translation initiation controls stress-induced gene expression in mammalian cells. Mol. Cell 6, 1099-1108.), and any target genes that can be identified by cDNA expression microarrays.
2) Increase of phosphorylation of eIF2α (Harding, H., Novoa, I., Zhang, Y., Zeng, H., Schapira, M., and Ron, D. (2000). Regulated translation initiation controls stress-induced gene expression in mammalian cells. Mol. Cell 6, 1099-1108).
3) Activation of the kinases that promote eIF2α phosphorylation.
4) Inhibition of dephosphorylation of phosphorylated eIF2α.

These various endpoints can be measured by anyone skilled in the art of cell biology using the following methods.

Activation of expression of any target genes or proteins can be assessed by determining either the level of transcription or the level of translation, in the presence of test substance in comparison with control assays performed in the absence of the test substance. Such assays may be performed on cells capable of expressing the target gene or a surrogate thereof, such as a reporter gene. The levels of phosphorylation of target proteins can be assessed by various methods, including immunoassays or radiolabeling.

TABLE 1

Target genes of the Integrated Stress Response identified by cDNA expression microarrays and Northern blot analysis

| Gene Name | Accession number (GenBank) |
| --- | --- |
| GLYT1 | W90900 |
| Cystathionine gamma-lyase | AA096870 |
| Methylenetetrahydrofolate dehydrogenase | W84014 |
| Serine Hydroxymethyltransferase | AA208877 |
| Heme Oxygnase-1 | AA213167 |
| XCTc | AA049696 |
| Coproporphyrinogen oxidase | AA259342 |
| CHOP | NM 007837 |
| GADD34 | |

TABLE 2

Target genes of the Integrated Stress Response (Genes with statistically significant reduced ER stress inducibility in PERK mutant cells)

| Gene Name(s) | Product/homology | Putative/known functional category | Accession number (GenBank) |
| --- | --- | --- | --- |
| Tj6 | vacuolar ATPase, proton pump homologue | secreted pathway function | AA881202 |
| Sec23b | homologue of Sec23b SEC23B (*S. cerevisiae*) | secreted pathway function | AI848343 |
| Ugalt, Had1 | UDP-galactose translocator 2 | secreted pathway function | D87990 |
| 1500026A19Rik | dolichyl-phosphate beta-glucosyltransferase homologue | secreted pathway function | AA111463 |
| Gpnat1 | Glucosamine-phosphate N-acetyltransferase 1 | secreted pathway function | AW123026 |
| Pig-a | GPI-anchor biosynthesis (PIG-A protein) | secreted pathway function | D31863 |
| Sel1h | Sel1 (suppressor of lin-12) 1 homolog (*C. elegans*) | secreted pathway function | AF063095 |
| Sel11 | negative regulator of Notch, promotes ERAD | secreted pathway function | AW121840 |
| WRN typeII | Werner syndrome homologue; helicase | stress response | D86527 |
| A170, STAP | oxidative stress inducible | stress response | U40930 |
| p58, Prkri, mp58 | interferon inducible PKR inhibitor, DnaJ (Hsp40) | stress response | U28423 |
| p58, Dnajc3 | interferon inducible PKR inhibitor, DnaJ (Hsp40) | stress response | U28423 |
| Dnajb9 | DnaJ (Hsp40) homologue, subfamily B, member 9 | stress response | AW120711 |
| mATF4 | Activating transcription factor 4 | transcription/stress response | M94087 |
| LRG-21, ATF3 | Activating transcription factor 3 | transcription/stress response | U19118 |

TABLE 2-continued

Target genes of the Integrated Stress Response
(Genes with statistically significant
reduced ER stress inducibility
in PERK mutant cells)

| Gene Name(s) | Product/homology | Putative/known functional category | Accession number (GenBank) |
| --- | --- | --- | --- |
| EST1 | alanine tRNA synthetase homologue | translation or amino acid metabolism | AI839392 |
| Wars | Tryptophanyl-tRNA synthetase | translation or amino acid metabolism | AI851163 |
| 1110068E11Rik | translation initiation factor eIF-4A -homologue | translation or amino acid metabolism | AW124530 |
| Rnu22 RNA | RNA, U22 small nucleolar | Ribosome biogenesis | AA684508 |
| GU2 | Nucleolar protein GU2, probable RNA helicase | Ribosome biogenesis | AA866971 |
| Snk | Serum-inducible kinase | signaling | M96163 |
| Fyn | proto-oncogene, tyrosine protein kinase | signaling | M27266 |
| 5730434I03Rik | BTF3 homologue (basal transcription factor) | transcription | AI846097 |
| Mpc2, Cbx4 | Chromobox homologue 4; transcriptional repressor | transcription | U63387 |
| Ets-2 | E26 avian leukemia oncogene 2, 3' domain | transcription | J04103 |
| c-myc | c-myc | transcription | L00039 |
| Arnt3, Bmal1 | CLOCK and NPAS2 dimer partner, regulated by NADH | transcription | AB014494 |
| E4BP4 | NFIL3/E4BP4 transcription, circadian rhythm regulated | transcription | U83148 |
| Etv6 | Ets variant gene 6 (TEL oncogene) | transcription | AI845538 |
| 2310004B05Rik | group XII secreted phospholipase A2 | secreted protein | AI845798 |
| EST2 | similar to extracellular matrix protein trichohyalin | secreted protein | AA612483 |
| Actb | Actb Actin, beta, cytoplasmic | cytoskelatin | M12481 |
| Ghitm | Growth hormone inducible transmembrane protein | growth/differen-tiation | AW120976 |
| EST3 | UCP2 mitochondrial uncoupling protein homologue | mitochondrial function | AW125634 |
| Rnula-1 | Small nuclear ribonucleoprotein polypeptide A | RNA/DNA housekeeping | L15447 |

Many experiments may be carried out to test the role of various components of the ISR activation pathway. For instance, the role of ATF4 may be analyzed using the following experiment. It is understood that appropriate experiments may be carried out to support the other known and yet determined components of the Integrated Stress Response.

ATF4−/− Cell Studies

ATF4−/− cells were explanted from mice that lack ATF4 (Hettmann, T., Barton, K., and Leiden, J. M. (2000). Microphthalmia due to p53-mediated apoptosis of anterior lens epithelial cells in mice lacking the CREB-2 transcription factor. Dev Biol 222, 110-23; Tanaka, T., Tsujimura, T., Takeda, K., Sugihara, A., Maekawa, A., Terada, N., Yoshida, N., and Akira, S. (1998). Targeted disruption of ATF4 discloses its essential role in the formation of eye lens fibres. Genes Cells 3, 801-10) and were maintained in media supplemented with 2 mM glutathione to protect them against oxidative stress. $1\times10^5$ cells per well were plated in 6 well dishes and grown in media containing 2 mM glutathione for 36 hours. At the indicated times prior to analysis, the glutathione-containing media was replaced with the same media lacking glutathione. (FIG. 2) 50 µM DCFH-DA (Molecular Probes) was added to the dishes 30 minutes before harvesting by trypsinization. The cells were collected in PBS containing 2% FCS by centrifugation and the cell pellet was resuspended in the same buffer containing 1 µg/ml propidium iodide (PI) (Roche) and FACScanned for the fluorescent signals emitted by the DCF in live cells and the PI fluorophores. FIG. 2, Part A, shows the fold-change in median DCF fluorescence, detected by FACS analysis in wildtype and ATF4−/− mouse fibroblasts after removal from protective, glutathione-containing media. FIG. 2, Part B, shows the percent of propidium iodide (PI) positive cells in the same samples shown in (A), indicating the loss of integrity of the cell membrane and cell death. ATF4−/− cells, that are defective in induction of the Integrated Stress Response, experience oxidative stress and cell death. This phenomena provides further support that the Integrated Stress Response promotes resistance to ROS.

Host cells

A broad variety of host-expression vector systems may be utilized to express the coding sequences of the proteins used in the assays of this invention. These include, but are not limited to, mammalian cell systems such as Cos-7, CHO, BHK, 3T3, HEK293. The mammalian cell systems may harbor recombinant expression constructs containing promoters derived from the genome of mammalian cells (e.g., metallothionein promoter) or from mammalian viruses (e.g., the adenovirus late promoter or the vaccine virus 7.5K promoter).

Additional host-expression vector systems include, but are not limited to, microorganisms such as bacteria (e.g., *E. coli* or *B. subtilis*) transformed with recombinant bacteriophage DNA, plasmid DNA, or cosmid DNA expression vectors containing PTK or adaptor protein coding sequences; yeast (e.g., Saccharomyces, Pichia) transformed with recombinant yeast expression vectors containing the protein or peptide coding sequences; insect cell systems, such as Sf9 or Sf21 infected with recombinant virus expression vectors (e.g., baculovirus) containing the protein or peptide coding sequences; amphibian cells, such as Xenopus oocytes; or plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein or peptide coding sequence. Culture conditions for each of these cell types is specific and is known to those familiar with the art.

In one example, COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$-Stock plates of COS-7 cells are trypsinized and split 1:6 every 3-4 days.

In another example, CHO cells are grown on 150 mm plates in HAM's F-12 medium with supplements (10% bovine calf serum, 4 mM L-glutamine and 100 units/ml penicillin/100 µg/ml streptomycin) at 37° C., 5% $CO_2$. Stock plates of CHO cells are trypsinized and split 1:8 every 3-4 days.

DNA encoding proteins to be assayed can be transiently or stably expressed in the cell lines by several methods known in the art, such as, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed.

In addition native cell lines that naturally carry and express the nucleic acid sequences for the target protein may be used.

Activation of Target Genes

The screening of test substances may be assessed by determining either the level of transcription of the target genes or the level of translation of the target proteins encoded by the genes, in the presence of the test substance. These target genes are herein identified as genes whose expression is modified in response to an oxidative stress. They include the target genes of Table 1, among which GADD34 plays a particular role: it acts as a stress-response gene that promotes resistance to stress, yet also exhibits negative feedback function in conjunction with PP1c as described herein. These target genes also include ATF4. The assays may be performed on cells capable of expressing the target gene or a surrogate thereof, such as a reporter gene.

Reporter gene assays of the invention may use one or more of the commonly used detection techniques involving isotopic, calorimetric, fluorimetric, or luminescent enzyme substrates and immuno-assay based procedures with isotopic, colorimetric, or chemiluminescent end points. The assays of the invention include, but are not limited to, using the reporter genes for the following proteins: CAT (chloramphenicol acetyltransferase, which transfers radioactive acetyl groups to chloramphenicol for detection by thin layer chromatography and autoradiography; GAL (β-galactosidase), which hydrolyzes colorless galactosides to yield colored products; GUS (β-glucuronidase), which hydrolyzes colorless glucuronides to yield colored product; LUC (luciferase), which oxidizes luciferin emitting photons; GFP (green fluorescent protein), which fluoresces on irradiation with UV; and hGH (human growth hormone), which is detected using a radioimmunoassay, and SEAP (a secreted form of the human placental alkaline phosphatase), which is detected with both calorimetric and chemiluminescent substrates.

Assays to monitor transcription of the target gene or the surrogate gene may be carried out by means of a Northern blot. Assays to monitor translation of the target gene or the surrogate gene may be carried out either by an immunoassay described herein or by utilizing the various read-outs for surrogate reporter genes described herein.

In one example, test substances, which activate CHOP are assayed with a surrogate reporter gene. Chinese Hamster Ovary cells (CHO) are stably transfected with the GFP reporter gene fused to the CHOP gene to form a CHOP:GFP CHO cell line (Wang, X. Z., Harding, H. P., Zhang, Y., Jolicoeur, E. M., Kuroda, M., and Ron, D. (1998). Cloning of mammalian Ire1 reveals diversity in the ER stress responses. EMBO J. 17, 5708-5717). This cell line may be treated with test compounds and the activity of the marker gene, GFP, may be monitored to identify compounds, which activate the Integrated Stress Response. In another embodiment, by substituting a LUC or GAL reporter for the GFP reporter, stably transfected CHO cells may be adapted for use in high throughput screening of libraries of compounds.

In another example, translation of ATF4 may be detected immunochemically in cultured cells exposed to test substances, by immunoblot or by immunocytochemistry described in the immunoassays herein, with antisera to ATF4. The antisera to ATF4 may also be adapted to an ELISA-based assay for measuring ATF4 expression, allowing high throughput screening for compounds that promote ATF4 translation.

In another embodiment, ATF4 translation may be detected by a surrogate assay using a stable cell line containing a reporter gene, such as LUC, controlled by the translational regulatory elements of the ATF4 mRNA (Harding, H., Novoa, I., Zhang, Y., Zeng, H., Schapira, M., and Ron, D. (2000). Regulated translation initiation controls stress-induced gene expression in mammalian cells. Mol. Cell 6, 1099-1108). The reporter gene is linked to all or part of the ATF4 promoter, in particular the ATF4 gene's translational regulatory sequences.

General Immunoassays

Various assays utilizing binding partners are useful in the screening methods of the invention. Preferably such binding partners are antibodies and the assays are called immunoassays. The below description refers to the use of antibodies, but it is understood that any other binding partner may be useful as well. Immunoassays are techniques known in the art, and include, for example, radioimmunoassay, ELISA (enzyme-linked immunosorbant assay), "sandwich" immunoassays, immunoradiometric assays, immunodiffusion assays, in situ immunoassays (using colloidal gold, enzyme or radioisotope labels, for example), western blots, precipitation reactions, immunofluorescence assays, and immunoelectrophoresis assays.

Monoclonal antibodies or polyclonal antibodies selective for the target protein are selected by techniques well known in the art. Immunoblots can be performed using lysates from cells that express the target protein to determine specificity. The preferred antibody will only bind to the target protein, preferably greater than 100,000 molecules per cell. An alternative method for determining specificity is immunoprecipitation. The binding affinity of the monoclonal antibody or polyclonal antibody for the substance can be determined by the relative strength of the signal generated in the immunoblot or by other techniques well known in the art.

A known number of cells expressing the target protein is lysed and serial dilutions of the lysate are applied to wells in a 96 well microtiter plate that have been precoated with the anchoring antibody. After allowing the substance to bind to the antibody, the unbound material is washed away and the amount of bound substance is determined using known immunoassay techniques. In order to have the proper signal to noise ratio one must be able to detect the target molecule in at least $1 \times 10^4$ cell equivalents per well. The maximum number of cells allowable per well is generally $<1 \times 10^5$ due to space constraints although this number may be somewhat larger or smaller depending on the cell type. The antibodies used in the immunoassays of the invention include, but are not limited, to polyclonal, monoclonal, chimeric, single chain, Fab fragments, and an Fab expression library.

For the production of antibodies, various host animals, including but not limited to rabbits, mice, rats may be immunized by injection with the particular antigen in a suitable adjuvant or by injecting the epitope conjugated to an immunogenic carrier. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique, which provides for the production of antibody molecules by continuous cell lines in culture. These include, but are not limited to, the hybridoma technique originally described by Koehler and Milstein, (Nature, 1975, 256:495-497), the human B-cell hybridoma technique (Kosbor et al., 1983, Immunology Today 4:72) and the EBV-hybridoma technique (Cole et al., 1985, Monoclonal Antibodies and Cancer Therapy, Alan R. Liss, Inc., pp. 77-96). Human antibodies may be used and can be obtained by using human hybridomas (Cote at al., 1983, Proc. Natl. Acad. Sci. 80:2026-2030) or by transforming human B cells with EBV virus in vitro (Cole et al., 1985, in, Monoclonal Antibodies and Cancer Therapy, Alan R. Liss, pp. 77-96). Techniques developed for the production of "chimeric antibodies" (Morrison et al., 1984, Proc. Natl. Acad. Sci. 81:6851-6855; Neuberger et al., 1984, Nature 312:604-608; Takeda et al., 1985, Nature 314:452-454) by splicing the genes from a mouse antibody molecule of appropriate antigen specificity together with genes from a human antibody molecule of appropriate biological activity can be used; such antibodies are within the scope of this invention.

Techniques for the production of single chain antibodies (U.S. Pat. No. 4,946,778) can also be used to produce substance-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity to antigens. Antibody fragments which contain binding sites specific for the protein of interest may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments.

The antibodies may be stored and purified using methods which are well known to those skilled in the art (e.g., see "Antibodies, A Laboratory-Manual", eds. Harlow & Lane, Cold Spring Harbor Laboratory, 1988, Ch. 8). Alternatively, polyclonal or monoclonal antibodies specific for the target protein may be obtained from commercial sources.

In the various immunoassays of the invention, antibody binding may be detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The immunoassays of the invention may be carried out using an immobilized phase. Solid phases used for the immobilization of a protein may be prepared by coating with the specific antibody. In the case where a polyclonal antibody is used, the solid phase may first be coated with an anti-Ig that binds to the polyclonal antibody and indirectly immobilizes it to the solid phase. The solid phase may comprise a microtiter plate, a stick, tube, disc, fiber or the like, or a microtiter plate. A preferred solid phase is a 96 well microtiter plate such as those available from Coming, Cynatech and Nunc. Particularly preferred 96 well plates are the Coming, Nunc MaxiSop and Dynatech Immulon I and IV. Ideal conditions for maximum coating can vary with pH, ionic strength and antibody concentration. Preferred conditions will be pH 6-9.5, 0-200 mM NaCl and 1-10 µg/ml of antibody. Generally 150 µl per well is used. The antibody may be attached to the solid phase by any of a variety of methods known to those skilled in the art, including but not limited to non-covalent and covalent attachments.

The antibody may be labeled directly or can be detected using a secondary reagent. Such signal generating systems include, but are not limited to, enzyme-linked systems (such as horseradish peroxidase or alkaline phosphatase), radiolabels, fluorescent labels, light-emitting labels, light-absorbing labels, dyes or biotin-avidin labeling systems (e.g., See "Antibodies, A Laboratory Manual, eds. Harlow & Lane, Cold Spring Harbor Laboratory 1988, Ch. 9).

In the case of conjugated enzymes, an appropriate substrate, such as a colorimetric substrate, is added. Specific substrates used for detection include ABTS (horseradish peroxidase), DAB, AEC, BCIP/NPT (alkaline phosphatase) and BCIG (beta-galactosidase). The binding of the enzyme-conjugated anti-IgG can be then detected quantitatively by techniques well known in the art.

cDNA Expression Microarrays to Determine New Target Genes

Target genes not yet identified may be determined using standard techniques well known in the art. Target genes include stress response genes and other genes upstream in the pathway. Knock-out mice PERK-/- allow the production of cell lines, which lack PERK (Harding, H., Zhang, Y., Bertolotti, A., Zeng, H., and Ron, D. (2000). Perk is essential for translational regulation and cell survival during the unfolded protein response. Mol. Cell 5, 897-904). PERK-/- cells and wild-type cells expressing PERK are exposed to tunicamycin (Sigma) that induces stress. Genes from the PERK−/− cell lines that are induced upon stress are determined utilizing cDNA expression microarrays (Affymetrix) and are compared with genes that are induced from wild type cell lines and identified by the same technique. The genes that are not induced upon stress in PERK−/− cells, but are induced in wild-type cells are considered as new target genes that are dependent on the Integrated Stress Response. They may be utilized in the methods described herein to identify test substances that activate the Integrated Stress Response.

In another embodiment, knock-out mice GCN2−/− allow the production of cell lines which lack GCN2 (Harding, H., Novoa, I., Zhang, Y., Zeng, H., Schapira, M., and Ron, D. (2000). Regulated translation initiation controls stress-induced gene expression in mammalian cells. Mol. Cell 6, 1099-1108). GCN2−/− cells and wild-type cells expressing GCN2 are exposed to media lacking the amino acid leucine inducing nutritional stress. Genes from the GCN2−/− cell lines that are induced upon stress are determined utilizing cDNA expression microarrays (Affymetrix) and are compared with genes that are induced from wild type cell lines and identified by the same technique. The genes that are not induced upon stress in GCN2−/− cells, but are induced in wild-type cells are considered as new target genes that are dependent on the Integrated Stress Response. They may be utilized in the methods described herein to identify test substances that activate the Integrated Stress Response.

In another embodiment, knock-out mice ATF4−/− allow the production of cell lines which lack ATF4 (Hettmann, T., Barton, K., and Leiden, J. M. (2000). Microphthalmia due to p53-mediated apoptosis of anterior lens epithelial cells in mice lacking the CREB-2 transcription factor. Dev Biol 222, 110-23.). ATF4−/− cells and wild-type cells expressing ATF4 are exposed to tunicamycin or media lacking the amino acid leucine or an oxidative stress causing agent such as arsenite, inducing stress. Genes from the ATF4−/− cell lines that are induced upon stress are determined utilizing cDNA expression microarrays (Affymetrix) and are compared with genes that are induced from wild type cell lines and identified by the same technique. The genes that are not induced upon stress in ATF4−/− cells, but are induced in wild-type cells are considered as new target genes that are dependent on the Integrated Stress Response. They may be utilized in the methods described herein to identify test substances that activate the Integrated Stress Response.

Measure of Phosphorylation of eIF2α and the Activation of Kinases

The levels of phosphorylation of target proteins can be assessed by various methods, including immunoassays or radiolabelling. Specifically, the increase of phosphorylation of EIF2α may be measured, activation of the kinases that promote eIF2α phosphorylation may be assayed, and inhibition of dephosphorylation of phosphorylated eIF2α may also be determined by these techniques.

In a preferred embodiment, the level of phosphorylation of a protein is assessed by utilizing a binding partner, which should be highly specific for the target protein. It is preferred that the binding partner be an antibody. It is preferably generated against a unique epitope of the substrate. In an alternative, the binding partner should be specific for the phosphorylated form of the target protein. The detection procedure used to assess the phosphorylation state of eIF2α may for instance employ an anti-phosphoserine antibody or a peptide that recognizes and binds to phosphorylated serines. The detection antibody is preferably a polyclonal antibody to maximize the signal, but may also be specific monoclonal antibodies which have been optimized for signal generation.

In one example, levels of eIF2α phosphorylated on serine 51 (in yeast eIF2α, corresponding to residue 52 in rodents or humans) can be measured by immunoblot or immunocytochemistry utilizing a commercially available antibodies, for example, product #9721 from Cell Signalling Technology. In one embodiment, the commercially available antisera to phosphorylated eIF2α may be used to develop high throughput screening assays for test substances that promote the accumulation of phosphorylated eIF2α.

In another example, inhibition of dephosphorylation of eIF2α on serine 51 (in yeast eIF2α, corresponding to residue 52 in rodents or humans) may be assayed by screening a test substance's ability to inhibit the activity of the PP1c and GADD34 complex (Novoa, I., Zeng, H., Harding, H., and Ron, D. (2001). Feedback inhibition of the unfolded protein response by GADD34-mediated dephosphorylation of eIF2α. J. Cell. Biol., in press). The PP1c and GADD34 complex is active in vitro, and its activity may be reconstituted using recombinant proteins. A cell-free assay may be used with the PP1c/Gadd34 complex in combination with phosphorylated eIF2α and test substances. By utilizing an ELISA assay, dephosphorylation of eIF2α by the PP1c/GADD34 complex and inhibition of this dephosphorylation by a test substance, may be monitored by measuring the decrease in phosphorylated eIF2α signal.

In a further example, activation of the eIF2α kinases, PERK, GCN2, HRI, and PKR, may be measured. Activation of the kinases is associated with an autophosphorylation event on known residues in the kinase (e.g., threonine 898 of mouse GCN2 and threonine 980 of mouse PERK). By using antisera, which recognize the phosphorylated and activated forms of the kinases, activation of the kinases may be detected using immunoblot or immunochemistry, such as with an ELISA. Antisera for the phosphorylated forms of the kinases PERK and GCN2 have been developed. (Harding, H., Novoa, I., Zhang, Y., Zeng, H., Schapira, M., and Ron, D. (2000). Regulated translation initiation controls stress-induced gene expression in mammalian cells. Mol. Cell 6, 1099-1108).

Alternatively, immunoassays may be replaced by the detection of radiolabeled phosphate according to a standard technique. This involves incubating cells with the test substances and radiolabeled phosphate, lysing the cells, separating cellular protein components of the lysate using as SDS-polyacrylamide gel (SDS-PAGE) technique, in either one or two dimensions, and detecting the presence of phosphorylated proteins by exposing X-ray film.

The phosphorylation of a protein may also be conveniently detected by migration on an electrophoresis gel and Western blot, to thereby observe whether a shift of the molecular weight of the protein occurs, a phosphorylated protein being heavier than the corresponding non-phosphorylated form.

Assays to Exclude Test Substances that Cause Stress

The above assays may be utilized to establish the site of action of the test substances. However, additional steps of verifying whether the test substances do not cause stress to the cells can be contemplated. For that purpose, one can measure the level of activation of other signalling proteins activated by ER stress, but not involved in the preconditioning pathway. More particularly, one can measure the level of phosphorylation of IRE1 (Bertolotti, A., Zhang, Y., Hendershot, L., Harding, H., and Ron, D. (2000). Dynamic interaction of BiP and the ER stress transducers in the unfolded protein response. Nature Cell Biology 2, 326-332; Harding, H., Zhang, Y., Bertolotti, A., Zeng, H., and Ron, D. (2000). Perk is essential for translational regulation and cell survival during the unfolded protein response. Mol Cell 5, 897-904), utilizing any standard method such as an immunoassay using an antibody specific for the phosphorylated form of the protein. One can also measure the cleavage of the protein called ATF6 (Wang, Y. et al., J. Biol. Chem., 2000, 275(35), 27013-27020), for example by tracking the appearance of the cleaved shorter forms of the protein on a Western blot.

In the case wherein the test substance is found to dissociate the PERK-BiP complex, one may also verify whether this dissociation is specific or whether it is indirectly caused by ER stress. This may be assayed by measuring the level of activation of other signalling proteins activated by ER stress, as mentioned herein, or by measuring the level of expression of BiP. Specifically, either the level of transcription or the level of translation of this chaperone protein is assessed. An increase in the level of expression of BiP is indicative of a stress, and therefore the test substances that promote such increases may be discarded as undesirable.

Similar considerations apply to the activation of GCN2. Test substances that indirectly activate GCN2 by causing a stress should be dismissed. For that purpose, one may assess whether the test substances promote the uncharging of tRNAs, which is undesirable. Established methods may be used (Dudek, S. M. et al., J. Biol. Chem., 1995, 270(49), 29323-29329). Specifically, the assay involves isolating tRNA, a fraction of which is charged with an amino acid and a fraction of which is not. One aliquot is oxidized, which prevents any initially uncharged tRNA from subsequently being acylated with an amino acid. Oxidation does not affect the ability of initially charged tRNA to be reacylated in vitro after the attached amino acid is removed, because the presence of the amino acid protects the 3' terminus of the tRNA from damage by periodate. A second aliquot is left unoxidized, allowing the determination of the total charging capacity of tRNA. The percentage of charged tRNA is determined by dividing the counts from in vitro charging reactions (using radiolabeled amino acids) using oxidized samples by the counts from reactions using unoxidized samples.

High Throughput Screening

The above assays may be performed using high throughput screening techniques for identifying test substances for developing drugs that, when added to cells, promote resistance to ROS without causing stress themselves. High throughput screening techniques may be carried out using multi-well plates (e.g., 96-, 389-, or 1536-well plates), in order to carry out multiple assays using an automated robotic system. Thus, large libraries of test substances may be assayed in a highly efficient manner.

A preferred strategy for identifying test substances starts with cultured cells transfected with a reporter gene fused to the promoter of any gene that is activated by the stress response pathway. More particularly, stably-transfected CHO cells growing in wells of micro-titer plates (96 well or 384 well) can be adapted to high through-put screening of libraries of compounds. The CHOP promoter is a preferable promoter due to its low basal activity. Libraries of test substances may be screened using this strategy. For example, the DIVERSET™ library of universally diverse, pre-designed 10,000-50,000 drug-like small molecules (ChemBridge Corporation, San Diego) may be used. Compounds in the library will be applied one at a time in an automated fashion to the wells of the microtitre dishes containing the transgenic cells described above. A compound that activates the reporter driven by the CHOP promoter will be identified and this particular compound will be subjected to secondary testing in one or all of the assays described herein. The composition and the structure of the identified test substances will be determined by referring back to the ChemBridge database. The test substance may be developed into a therapeutic agent to prevent or treat a disease caused by oxidative stress.

Once the test substances which activate one of the target genes are identified, it is preferable to then determine their site of action in the Integrated Stress Response pathway. It is particularly useful to define the site of action for the development of more refined assays for in order to optimize the target substance. Assays to determine the site of action of the target substance in the ISR may be carried out using high throughput techniques.

The ELISA-based assay for measuring ATF4 translation is particularly adapted to rapid high throughput screening. Similarly, an ELISA assay for measuring phosphorylated eIF2α, by means of commercially available antiserum, may be developed for high throughput screening. Alternatively, antisera to phorphorylated eIF2α kinases may be advantageously used in ELISA-based high throughput screens to focus on upstream components of the pathway.

ELISA-type assays may be performed in microtitre plates. See, for example, Peraldi et al., 1992, J. Biochem. 285: 71-78; Schraag, et al., 1993, Analytical Biochemistry 211: 233-239; Cleavland, 1990, Analytical Biochemistry 190: 249-253; Farley, 1992, Analytical Biochemistry 203: 151-157; and Lczaro, 1991, Analytical Biochemistry 192: 257-261. For evaluating the effects of a test substance on phosphorylation within the normal cellular context, one can also used the rapid and quantitative assays systems described in U.S. Pat. No. 5,763,198. For example, two embodiments may be contemplated as follows.

The extent of phosphorylation of a target protein may be measured by exposing cells that express the target protein to a test substance and, thereafter, lysing the cell to release the cellular contents. The target protein is isolated by incubating the cell lysate with a binding partner to a solid support and thereafter washing away non-bound cellular components. A detection procedure is performed to assess the presence or absence of phosphorylated residues on the protein as compared to lysates of control cells, which were not exposed to the test substance. Alternatively, the binding partner may be directed against the phosphorylated forms of the target protein, so that the steps of isolation and of detection of phosphorylation are performed simultaneously.

These assays offer several advantages. The exposure of the test substance to a whole cell allows for the evaluation of its activity in the natural context in which the test substance may act. In addition, radioactive labeling of the target cell proteins is not required in the assay. Because this assay can readily be performed in a microtitre plate format, the assays described can be performed by an automated robotic system, allowing for testing of large numbers of test samples within a reasonably short time frame.

An alternative embodiment of the invention relates to methods for determining the effect of a test substance on the ability of kinases to phosphorylate eIF2α in a cell-free system. To assess modulation of enzyme activity, the test substance is added to a reaction mixture containing the kinase and eIF2α bound to a solid support by an antibody. The kinase reaction may be initiated by the addition of ATP.

A detection procedure as described herein is performed on the substance to assess the presence or absence of the phosphorylated residues, and results are compared to those obtained for controls, i.e., reaction mixtures to which the test substance was not added.

The assays of the invention can be used as a screen to assess the activity of a previously untested compound or extract, in which case a single concentration is tested and compared to controls. These assays can also be used to assess the relative potency of a compound by testing a range of concentrations, in a range of 100 µM to 1 pM, for example, and computing the concentration at which the amount of phosphorylation is increased by one-half (IC50) compared to controls.

The whole cell assay of the invention described herein can be performed, for example, by utilizing pre-packaged kits comprising any or all of the reagents of the assay, such as a solid phase coated with a binding partner to a protein of interest, or a detection molecule. The cell-free assays of the invention may be performed, for example, by utilizing pre-packaged kits comprising any or all of the reagents of the assay.

High Throughput Screening Example

CHO K1 cells may be obtained from ATCC and may be cultured in DMEM:F12 in the presence of 10% fetal calf serum (Atlantic Biological). A murine CHOP genomic fragment containing the CHOP promoter may be used. The fragment is 8.5 kb in length, wherein its 3' end corresponds to the Pm/I site in exon 3, nine nucleotides 5' to the initiation methionine of CHOP. CHO K1 cells may be transfected with the CHOP genomic fragment linked to the GFP reporter gene by the Lipofectamine plus method (Gibco-BRL) using 1 µg plasmid DNA per 35 mm plate. Cells may plated 48 hours after transfection to form CHOP-GFP transient reporter cells. Alternatively, the transfection of the reporter plasmid may include 0.1 µg of the $Neo^r$-containing plasmid pCDNA3 (Invitrogen) followed by selection of transfected cells with 0.5 mg/ml of the aminoglycosidic antibiotic G418 (Fisher Scientific) for 10 days to establish stable clones containing the reporter.

CHOP-GFP reporter cells are plated into 96 well microtitre plates at $5 \times 10^3$ cells per well. Individual compounds (test substances) from the DIVERSet™ library, a library of universally diverse, pre-designed 10,000-50,000 drug-like small molecules (ChemBridge Co.), may be tested. The test substances would be added one at a time in an automated fashion at concentrations from $10^{-9}$ M to $10^{-6}$ M to the wells of the microtitre dishes containing the CHOP-GFP reporter cells. Test substances that activate the CHOP gene are identified through fluorescence of the GFP reporter protein using FL600 Microplate Fluorescence and Absorbance Reader (Bio Tek).

The invention is thus directed to a method for identifying a test substance useful for the prevention or treatment of a disease involving an oxidative stress, which comprises testing the substance for its ability to promote resistance to cell stress while not causing stress, so as to thereby determine whether said substance is effective as a preventive or therapeutic agent for a disease involving an oxidative stress.

The invention is directed to a method for screening a plurality of test substances useful for the prevention or treatment of a disease involving an oxidative stress, which comprises the steps of i) testing each of the test substances for its ability to activate the expression of CHOP gene, and ii) identifying the test substance which activates the expression of CHOP, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of CHOP gene, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. In another embodiment, the method comprises the steps of i) contacting the test substance or each of the test substances with a cell transfected with a reporter gene operatively linked to all or part of the promoter of the CHOP gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing the CHOP gene, ii) assessing the level of expression of said gene, and iii) identifying the test substance which activates the expression of said gene, thereby to identify a test substance useful as a preventive or therapeutic agent for a disease involving ran oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In another embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of GLYT1 gene, and ii) identifying the test substance which activates the expression of GLYT1, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of GLYT1 gene, thereby to determine whether the substance promotes resistance to cell stress, and to identify said substance as a preventive or therapeutic agent for a disease involving an oxidative stress. In one embodiment, the invention further comprises a step of verifying whether said test substance does not cause stress to cells. In a further embodiment, the method comprises the steps of i) contacting the test substance or each of the test substances with a cell transfected with a reporter gene operatively linked to all or part of the promoter of the GLYT1 gene, ii) assessing the level of expression of said reporter gene, and iii) identifying the test substance which activates the expression of said reporter gene, thereby to identify a test substance useful as a preventive or therapeutic agent for a disease involving an oxidative stress. In another embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing the GLYT1 gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by the level of translation of said gene. In a further embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of cystathionine gamma-lyase, and ii) identifying the test substance which activates the expression of cystathionine gamma-lyase, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of cystathionine gamma-lyase, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. In another embodiment, the method comprises the steps of i) contacting the test substance or each of the test substances with a cell transfected with a reporter gene operatively linked to all or part of the promoter of the cystathionine gamma-lyase gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing cystathionine gamma-lyase gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of methylenetetrahydrofolate dehydrogenase, and ii) identifying the test substance which activates the expression of methylenetetrahydrofolate dehydrogenase, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of methylenetetrahydrofolate dehydrogenase, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. In another embodiment, the method comprises the steps of i) contacting the test substance or each of the test substances with a cell transfected with a reporter gene operatively linked to all or part of the promoter of the methylenetetrahydrofolate dehydrogenase gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing the methylenetetrahydrofolate dehydrogenase gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of serine hydroxymethyltransferase, and ii) identifying the test substance which activates the expression of serine hydroxymethyltransferase, thereby to identify a test substance useful as a preventive or therapeutic agent for a disease involving an oxidative stress. The invention is further directed to a method for identifying a test substance useful for the prevention or treatment of a disease involving an oxidative stress, which comprises testing a test substance for its ability to activate the expression of serine hydroxymethyltransferase, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. In another embodiment, the method comprises the steps of i) contacting the test substance or each of the test substances with a cell transfected with a reporter gene operatively linked to all or part of the promoter of the serine hydroxymethyltransferase gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to the method, which comprises the steps of i) contacting the test substance or each of the test substances with a cell capable of expressing the serine hydroxymethyltransferase gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In another embodiment, the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of heme oxygenase-1, and ii) identifying the test substance which activates the expression of heme oxygenase-1, thereby to identify a test substance useful as a preventive or therapeutic agent for a disease involving an oxidative stress. The method is further directed to a method for identifying a test substance useful for the prevention or treatment of a disease involving an oxidative stress, which comprises testing a test substance for its ability to activate the expression of heme oxygenase-1, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. In another embodiment, the method comprises the steps of i) contacting the test substance or each of the test substances with a cell transfected with a reporter gene operatively linked to all or part of the promoter of the heme oxygenase-1 gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing the heme oxygenase-1 gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of XCTc gene, and ii) identifying the test substance which activates the expression of XCTc gene, thereby to identify a test substance useful as a preventive or therapeutic agent for a disease involving an oxidative stress. The invention is further drawn to a method for identifying a test substance useful for the prevention or treatment of a disease involving an oxidative stress, which comprises testing a test substance for its ability to activate the expression of XCTc gene, thereby to determine whether the substance promotes resistance to cell stress, and to identify said substance as a preventive or therapeutic agent for a disease involving an oxidative stress. In one embodiment, the method comprises a step of verifying whether said test substance does not cause stress to cells. In another embodiment, the method comprises the steps of i) contacting the test substance or each of the test substances with a cell transfected with a reporter gene operatively linked to all or part of the promoter of the XCTc gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to the method, which comprises the steps of i) contacting the test substance or each of the test substances with a cell capable of expressing the XCTc gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of coproporphyrinogen oxidase, and ii) identifying the test substance which activates the expression of coproporphyrinogen oxidase, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of coproporphyrinogen oxidase, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. In another embodiment, the method comprises the steps of i) contacting the test substance or each of the test substances with a cell transfected with a reporter gene operatively linked to all or part of the promoter of the coproporphyrinogen oxidase gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing the coproporphyrinogen oxidase gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of a target gene, wherein the target gene is selected from the group consisting of Tj6 gene, Sec23b gene, Ugalt gene, 1500026A19Rik gene, Gpnat1 gene, Pig-a gene, Sel1h gene, Sel11 gene, WRN typeII gene, A170 gene, Prkri gene, Dnajc3 gene, Dnajb9 gene, mATF4 gene, LRG-21 gene, EST1 gene, Wars gene, 1110068E11Rik gene, Rnu22 RNA gene, GU2 gene, Snk gene, Fyn gene, 5730434I03RiK gene, Rnu22 RNA gene, GU2 gene, Snk gene, Fyn gene, 5730434103Rik gene, Mpc2 gene, Ets-2 gene, c-myc gene, Arnt3 gene, E4BP4 gene, Etv6 gene, 2310004B05Rik gene, EST2 gene, Actb gene, Ghitm gene, EST3 gene, and Rnu1a-1 gene, and ii) identifying the test substance which activates the expression of the target gene, thereby to identify a test substance useful as a preventive or therapeutic agent for a disease involving an oxidative stress. The invention is further directed to a method for identifying a test substance useful for the prevention or treatment of a disease involving an oxidative stress, which comprises testing a test substance for its ability to activate the expression of a target gene, wherein the target gene is selected from the group consisting of Tj6 gene, Sec23b gene, Ugalt gene, 1500026A19Rik gene, Gpnat1 gene, Pig-a gene, Sel1h gene, Sel11 gene, WRN typeII gene, A170 gene, Prkri gene, Dnajc3 gene, Dnajb9 gene, mATF4 gene, LRG-21 gene, EST1 gene, Wars gene, 1110068E11Rik gene, Rnu22 RNA gene, GU2 gene, Snk gene, Fyn gene, 5730434I03RiK gene, Rnu22 RNA gene, GU2 gene, Snk gene, Fyn gene, 5730434I03Rik gene, Mpc2 gene, Ets-2 gene, c-myc gene, Arnt3 gene, E4BP4 gene, Etv6 gene, 2310004B05Rik gene, EST2 gene, Actb gene, Ghitm gene, EST3 gene, and Rnu1a-1 gene, thereby to determine whether the substance promotes resistance to cell stress, and to identify said substance as a preventive or therapeutic agent for a disease involving an oxidative stress.

In one embodiment, the method further comprises a step of verifying whether said test substance does not cause stress to cells. In a further embodiment, the method comprises the steps of i) contacting the test substance or each of the test substances with a cell transfected with a reporter gene operatively linked to all or part of the promoter of the target gene, ii) assessing the level of expression of said reporter gene, and iii) identifying the test substance which activates the expression of said reporter gene, thereby to identify a test substance useful as a preventive or therapeutic agent for a disease involving an oxidative stress. In a further embodiment, the reporter gene encodes one of the group consisting of GFP, CAT, GAL, LUC, and GUS. In another embodiment, the cell is one of the group consisting of a CHO, BHK, 3T3, and HEK293 cell line.

In one embodiment, the method comprises the steps of i) contacting the test substance or each of the test substances with a cell capable of expressing the target gene, ii) assessing the level of expression of said gene, and iii) identifying the test substance which activates the expression of said gene, thereby to identify a test substance useful as a preventive or therapeutic agent for a disease involving an oxidative stress. In a further embodiment, the level of expression is assessed by determining the level of transcription of said gene. In another embodiment, the determination of the level of transcription of said gene is effected by means of a Northern blot. In another embodiment, the level of expression is assessed by determining the level of translation of said gene. In a further embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of a target gene, wherein said target gene may be identified in a assay comprising submitting a cell to stressful conditions and determining the genes whose transcription is enhanced in the presence of an active PERK protein and not enhanced or inhibited in the absence of such active PERK protein, and ii) identifying the test substance which activates the expression of said target gene, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of a target gene, wherein said target gene may be identified in a assay comprising submitting a cell to stressful conditions and determining the genes whose transcription is enhanced in the presence of an active PERK protein and not enhanced or inhibited in the absence of such active PERK protein, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells.

The invention is directed to the method, which comprises the steps of i) contacting the test substance or each of the test substances with a cell transfected with a reporter gene operatively linked to all or part of the promoter of said target gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing said target gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of a target gene, wherein said target gene may be identified in a assay comprising submitting a cell to stressful conditions and determining the genes whose transcription is enhanced in the presence of an active GCN2 protein and not enhanced or inhibited in the absence of such active GCN2 protein, and ii) identifying the test substance which activates the expression of said target gene, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of a target gene, wherein said target gene may be identified in a assay comprising submitting a cell to stressful conditions and determining the genes whose transcription is enhanced in the presence of an active GCN2 protein and not enhanced or inhibited in the absence of such active GCN2 protein, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells.

The invention is directed to the method, which comprises the steps of i) contacting the test substance or each of the test substances with a cell transfected with a reporter gene operatively linked to all or part of the promoter of said target gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing said target gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of a target gene, wherein said target gene may be identified in a assay comprising submitting a cell to stressful conditions and determining the genes whose transcription is enhanced in the presence of an active ATF4 protein and not enhanced or inhibited in the absence of such active ATF4 protein, and ii) identifying the test substance which activates the expression of said target gene, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of a target gene, wherein said target gene may be identified in a assay comprising submitting a cell to stressful conditions and determining the genes whose transcription is enhanced in the presence of an active ATF4 protein and not enhanced or inhibited in the absence of such active ATF4 protein, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells.

The invention is directed to the method, which comprises the steps of i) contacting the test substance or each of the test substances with a cell transfected with a reporter gene operatively linked to all or part of the promoter of said target gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing said target gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to activate the expression of ATF4 gene, and ii) identifying the test substance which activates the expression of ATF4, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate the expression of ATF4 gene, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. The invention is directed to a method, which comprises the steps of i) contacting the test substance or each of the test substances with a cell transfected with a reporter gene operatively linked to all or part of the promoter of the ATF4 gene, ii) assessing the level of expression of said reporter gene, and iii) identifying the test substance which activates the expression of said reporter gene, thereby to identify a test substance useful as a preventive or therapeutic agent for a disease involving an oxidative stress. In one embodiment, the reporter gene encodes one of the group consisting of GFP, CAT, GAL, LUC, and GUS. In another embodiment, the cell is one of the group consisting of a CHO, BHK, 3T3, and HEK293 cell line.

The invention is directed to a method, which comprises the steps of i) contacting the test substance or each of the test substances with a cell capable of expressing the ATF4 gene, ii) assessing the level of expression of said gene, and iii) identifying the test substance which activates the expression of said gene, thereby to identify a test substance useful as a preventive or therapeutic agent for a disease involving an oxidative stress. In one embodiment, the level of expression is assessed by determining the level of transcription of said gene. In a further embodiment, the determination of the level of transcription of said gene is effected by means of a Northern blot. In another embodiment, the level of expression is assessed by determining the level of translation of said gene. In a further embodiment, the determination of the level of translation of said gene is effected by means of an immunoassay.

The invention is directed to a method for screening a plurality of test substances useful for the prevention or treatment of a disease involving an oxidative stress, which comprises the steps of i) testing each of the test substances for its ability to increase phosphorylation of eIF2α, and ii) identifying the test substance which increases phosphorylation of eIF2α, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to increase phosphorylation of eIF2α, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells.

The invention is directed to the method, which comprises the steps of i) contacting the test substance or each of the test substances with a cell capable of expressing eIF2α, ii) assessing the level of phosphorylation of eIF2α, and iii) identifying the test substance which increases the phosphorylation of eIF2α, thereby to identify a test substance useful as a preventive or therapeutic agent for a disease involving an oxidative stress. In one embodiment, the assessment of the level of phosphorylation of eIF2α is effected by an immunoassay using an antibody that specifically recognizes the phosphorylated form of eIF2α. In another embodiment, the assessment of the level of phosphorylation of eIF2α is effected by tracking the covalent binding of a radiolabeled phosphate group to eIF2α.

The invention is directed to a method for screening a plurality of test substances useful for the prevention or treatment of a disease involving an oxidative stress, which comprises the steps of i) testing each of the test substances for its ability to inhibit the dephosphorylation of eIF2α, and ii) identifying the test substance which inhibits the dephosphorylation of eIF2α, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to inhibit the dephosphorylation of eIF2α, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells.

The invention is directed to a method, which comprises the steps of i) contacting the test substance or each of the test substances with a cell-free composition containing GADD34 and PP1c proteins in the form of a purified complex and eIF2α in a phosphorylated form, ii) assessing the level of phosphorylation of eIF2α, in comparison with the level of phosphorylation determined in the absence of test substances, in a cell-free composition containing GADD34 and PP1c proteins in the form of a purified complex and eIF2α in a phosphorylated form, and iii) identifying the test substance which provides a higher level of phosphorylation of eIF2α, in comparison with the level of phosphorylation determined in the absence of test substance, thereby to identify a test substance useful as a preventive or therapeutic agent for a disease involving an oxidative stress. In one embodiment, the assessment of the level of phosphorylation of eIF2α is effected by an immunoassay using an antibody that specifically recognizes the phosphorylated form of eIF2α. In another embodiment, the assessment of the level of phosphorylation of eIF2α is effected by tracking the covalent binding of a radiolabeled phosphate group to eIF2α.

The invention is directed to a method for screening a plurality of test substances useful for the prevention or treatment of a disease involving an oxidative stress, which comprises the steps of i) testing each of the test substances for its ability to activate an eIF2α kinase and ii) identifying the test substance which activates an eIF2α kinase, thereby to identify a test substance useful as a preventive or therapeutic agent for a disease involving an oxidative stress. The invention is also directed to a method for identifying a test substance useful for the prevention or treatment of a disease involving an oxidative stress, which comprises testing a test substance for its ability to activate an eIF2α kinase, thereby to determine whether the substance promotes resistance to cell stress, and to identify said substance as a preventive or therapeutic agent for a disease involving an oxidative stress. In one embodiment, the method further comprises a step of verifying whether said test substance does not cause stress to cells. In one embodiment, the kinase is PERK. In one embodiment, the kinase is GCN2. In another embodiment, the kinase is HRI. In a further embodiment, the kinase is PKR.

The invention is directed to a method, which comprises the steps of i) contacting the test substance or each of the test substances with a cell capable of expressing said eIF2α kinase, ii) assessing the level of phosphorylation of said eIF2α kinase, and iii) identifying the test substance which triggers the phosphorylation of said eIF2α kinase thereby to identify a test substance useful as a preventive or therapeutic agent for a disease involving an oxidative stress. In one embodiment, the assessment of the level of phosphorylation of eIF2α is effected by an immunoassay using an antibody that specifically recognizes the phosphorylated form of said eIF2α kinase. In another embodiment, the assessment of the level of phosphorylation of eIF2α is effected by tracking the covalent binding of a radiolabeled phosphate group to said eIF2α kinase. In another embodiment, the method comprises the steps of i) contacting the test substance or each of the test substances with a cell capable of expressing PERK and BiP in the form of a complex, ii) assessing the dissociation of the PERK-BiP complex, and iii) identifying the test substance which triggers the disruption of the PERK-BiP complex, whereby PERK is rendered active, thereby to identify a test substance useful as a preventive or therapeutic agent for a disease involving an oxidative stress. In another embodiment, the method further comprises the steps of measuring the level of expression of BiP and identifying the test substance that does not enhance the expression of BiP, to thereby identify a test substance that does not cause stress and is useful as a preventive or therapeutic agent for a disease involving an oxidative stress. In another embodiment, the method further comprises the steps of measuring the level of activation of IRE1 and ATF6 and identifying the test substances that do not activate IRE1 and ATF6, to thereby identify a test substance that does not cause stress and is useful as a preventive or therapeutic agent for disease involving oxidative stress. In another embodiment, wherein the kinase is GCN2, the method further comprises the steps of measuring the charging of tRNAs, and identifying the test substances that do not lead to uncharged tRNAs, to thereby identify a test substance that does not cause stress and is useful as a preventive or therapeutic agent for disease involving oxidative stress.

The invention is directed to the above methods, wherein the selected test substance is potentially useful for the prevention or treatment of a disease involving neuronal ischemia. The invention is further directed to the above methods, wherein the selected test substance is potentially useful for the prevention or treatment of a disease involving heart ischemia. The invention is directed to the above methods, wherein the selected test substance is potentially useful for the prevention or treatment of a renal damage induced by ischemia or toxins. The invention is also directed to the above methods, wherein the selected test substance is potentially useful for the prevention or treatment of a auto-immune disease. The invention is further directed to the above methods, wherein the selected test substance is potentially useful for the prevention or treatment of a neurodegenerative disorder.

The invention is also directed to a pharmaceutical composition, comprising a therapeutic agent identified as being capable of promoting resistance to cell stress while not causing stress, in association with a pharmaceutically acceptable carrier. This therapeutic agent is defined as a substance that can activate the expression of a target gene of the Integrated Stress Response pathway, while not being toxic, which means more particularly that it does not cause stress to the cell. These properties may be determined by the methods of screening as above described.

The invention is further directed to a method for the prevention or treatment of a disease involving an oxidative stress in a patient in need of such treatment, which comprises administering to the patient an effective amount of a therapeutic agent, identified for its ability to promote resistance to cell stress while not causing stress. In one embodiment, the therapeutic agent is identified as useful for the prevention or treatment of a disease involving oxidative stress, which comprises testing the therapeutic agent for its ability to trigger phosphorylation of eIF2α, thereby to determine whether the therapeutic agent promotes resistance to cell stress. This disease may be a disease involving neuronal ischemia, or a disease involving heart ischemia. It may also involve renal damage induced by ischemia or toxins. It may additionally be an auto-immune disease or a neurodegenerative disorder.

Therapeutic agents that promote preconditioning and may be developed by this platform technology may more particularly prevent cognitive and neurological dysfunction in patients undergoing cardio-pulmonary bypass, if administered prophylactically or during the procedure. They may also protect the myocardium, kidneys and intestine from damage incurred during cardio-pulmonary bypass. Such therapeutic agents may also be efficacious in circumstances where neurological damage by ROS may be anticipated, such as early in the course of head trauma, in the post-neurosurgery period, following surgical procedures for brain re-vascularization, or in the treatment of status epilepticus.

The therapeutic agents may be administered locally to preserve function of specific organs that are to be subjected to ischemic stress. For example, intracoronary instillation to preserve myocardial function in preparation of cardiac surgery, or injection into the renal artery to preserve kidney function in preparation for surgery on the abdominal aorta.

Therapeutic agents developed by this platform technology may be used ex-vivo in the preservation of organs and cells procured for purpose of transplantation from live or cadaver donors. For example, the essential role of PERK in promoting survival of pancreatic islets of Langerhans suggests that activating the ISR will promote survival of such cells ex-vivo and extend their utility in transplantation therapy of Diabetes Mellitus.

This platform technology may also be useful for identifying lead compounds for drug development to treat chronic diseases associated with cell and tissue damage caused by ROS. Examples of such conditions include Diabetes Mellitus, Parkinson's Disease and Cirrhosis.

What is claimed is:

1. A method for screening a plurality of test substances to identify a substance useful as a substance that promotes resistance to cell stress, which comprises the steps of
   i) testing each of the test substances for its ability to activate the expression of a higher eukaryote target gene of the Integrated Stress Response by contacting each of the test substances with a higher eukaryote cell capable of expressing the CHOP gene,
   ii) identifying the test substance which activates the expression of the higher-eukaryote target gene of the Integrated Stress Response by assessing the level of expression of said higher eukaryote target gene of the Integrated Stress Response wherein the level of expression is assessed by determining the level of transcription or translation of said CHOP gene thereby to identify a substance useful as a substance that promotes resistance to cell stress; and
   iii) verifying that said test substance does not cause stress to higher eukaryote cells, thereby identifying a substance useful as a substance that promotes resistance to cell stress.

2. The method according to claim 1, wherein determination of the level of transcription of said CHOP gene is effected by means of a Northern blot.

3. The method according to claim 1, wherein determination of the level of translation of said CHOP gene is effected by means of an immunoassay.

4. A method for identifying a substance useful as a substance that promotes resistance to cell stress, which comprises
   i) testing a test substance for its ability to activate the expression of a higher eukaryote target gene of the Integrated Stress Response by contacting the test substance with a higher eukaryote cell capable of expressing the CHOP gene,
   ii) assessing the level of expression of said higher eukaryote target gene of the Integrated Stress Response, wherein the level of expression is assessed by determining the level of transcription of or translation said CHOP gene;
   iii) identifying the test substance which activates the expression of said CHOP gene, thereby to identify a substance useful as a substance that promotes resistance to cell stress; and
   iv) verifying that said test substance does not cause stress to higher eukaryote cells, thereby identifying a substance useful as a substance that promotes resistance to cell stress.

5. The method according to claim 4, wherein determination of the level of transcription of said CHOP gene is effected by means of a Northern blot.

6. The method according to claim 4, wherein determination of the level of translation of said CHOP gene is effected by means of an immunoassay.

* * * * *